US008246940B2

(12) United States Patent
Marie et al.

(10) Patent No.: US 8,246,940 B2
(45) Date of Patent: Aug. 21, 2012

(54) COSMETIC COMPOSITION COMPRISING GELLAN GUM OR A DERIVATIVE THEREOF, A FIXING POLYMER, A MONOVALENT SALT AND AN ALCOHOL, PROCESS OF USING THE SAME

(75) Inventors: Laurence Marie, Saint-Denis (FR); Ludivine Laurent, Courbevoie (FR); Dorothée Pasquet, Bois-Colombes (FR); Marie-Laure Breton, Paris (FR)

(73) Assignee: L'Oreal S.A., Paris (FR)

( * ) Notice: Subject to any disclaimer, the term of this patent is extended or adjusted under 35 U.S.C. 154(b) by 877 days.

(21) Appl. No.: 10/990,516

(22) Filed: Nov. 18, 2004

(65) Prior Publication Data
US 2005/0129650 A1    Jun. 16, 2005

Related U.S. Application Data

(60) Provisional application No. 60/562,317, filed on Apr. 15, 2004.

(30) Foreign Application Priority Data

Nov. 18, 2003 (FR) ..................... 03 13486

(51) Int. Cl.
*A61Q 5/06* (2006.01)
*A61Q 5/12* (2006.01)
*A61Q 1/00* (2006.01)

(52) U.S. Cl. ............... 424/70.16; 424/47; 424/70.11

(58) Field of Classification Search .............. None
See application file for complete search history.

(56) References Cited

U.S. PATENT DOCUMENTS

| | | | |
|---|---|---|---|
| 2,047,398 A | 7/1936 | Voss et al. | |
| 2,723,248 A | 11/1955 | Wright | |
| 3,810,977 A | 5/1974 | Levine et al. | |
| 3,836,537 A | 9/1974 | Boerwinkle et al. | |
| 3,910,862 A | 10/1975 | Barabas et al. | |
| 3,925,542 A | 12/1975 | Viout et al. | |
| 3,946,749 A | 3/1976 | Papantoniou | |
| 3,966,403 A | 6/1976 | Papantoniou et al. | |
| 3,966,404 A | 6/1976 | Papantoniou et al. | |
| 3,990,459 A | 11/1976 | Papantoniou | |
| 4,031,307 A | 6/1977 | DeMartino et al. | |
| 4,070,533 A | 1/1978 | Papantoniou et al. | |
| 4,076,912 A | 2/1978 | Papantoniou et al. | |
| 4,128,631 A | 12/1978 | Lundmark et al. | |
| 4,129,711 A | 12/1978 | Viout et al. | |
| 4,131,576 A | 12/1978 | Iovine et al. | |
| 4,137,208 A | 1/1979 | Elliott | |
| 4,165,367 A | 8/1979 | Chakrabarti | |
| 4,223,009 A | 9/1980 | Chakrabarti | |
| 4,282,203 A | 8/1981 | Jacquet et al. | |
| 4,289,752 A | 9/1981 | Mahieu et al. | |
| 4,693,935 A | 9/1987 | Mazurek | |
| 4,728,571 A | 3/1988 | Clemens et al. | |
| 4,844,889 A * | 7/1989 | Papantoniou et al. ....... | 424/70.9 |
| 4,972,037 A | 11/1990 | Garbe et al. | |
| 5,190,927 A * | 3/1993 | Chang et al. ..................... | 514/54 |
| 5,523,078 A | 6/1996 | Baylin | |
| 5,538,717 A | 7/1996 | De La Poterie | |
| 5,690,921 A * | 11/1997 | Lang et al. .................. | 424/70.13 |
| 5,879,669 A * | 3/1999 | Clausen et al. ............ | 424/70.11 |
| 6,106,813 A | 8/2000 | Mondet et al. | |
| 6,110,473 A | 8/2000 | Fitzpatrick et al. | |
| 6,126,930 A | 10/2000 | Dubois et al. | |
| 6,166,093 A | 12/2000 | Mougin et al. | |
| 6,180,122 B1 | 1/2001 | Roulier et al. | |
| 6,319,959 B1 | 11/2001 | Mougin et al. | |
| 6,372,876 B1 | 4/2002 | Kim et al. | |
| 6,391,288 B1 | 5/2002 | Miyazawa et al. | |
| 6,395,265 B1 | 5/2002 | Mougin et al. | |
| 6,399,050 B1 * | 6/2002 | Pasquet et al. ............. | 424/70.12 |
| 6,624,125 B2 | 9/2003 | Trage et al. | |
| 6,630,133 B1 * | 10/2003 | Dupuis ........................ | 424/70.1 |
| 6,770,271 B2 | 8/2004 | Modet et al. | |
| 2002/0144356 A1 | 10/2002 | Kawai et al. | |
| 2002/0150546 A1 | 10/2002 | Mougin et al. | |
| 2003/0033678 A1 | 2/2003 | Schulze zur Wiesche et al. | |
| 2003/0072779 A1 | 4/2003 | Sato et al. | |

FOREIGN PATENT DOCUMENTS

| | | |
|---|---|---|
| DE | 2 330 956 | 1/1974 |
| EP | 0 080 976 | 6/1983 |
| EP | 0 412 704 | 2/1991 |
| EP | 0 412 707 | 2/1991 |
| EP | 0 582 152 | 2/1994 |
| EP | 0 619 111 | 10/1994 |
| EP | 0 637 600 | 2/1995 |
| EP | 0 985 410 | 3/2000 |
| EP | 1062936 | * 12/2000 |
| EP | 1085695 | * 3/2001 |
| GB | 839805 | 6/1960 |
| GB | 922457 | 4/1963 |
| GB | 1021400 | 3/1966 |

(Continued)

OTHER PUBLICATIONS

English Language Abstract of JP 02144067.
English Language Abstract of JP 11335691.
English Language Abstract of JP 09020649.
Edward P. Duliba et al. "Clarified high acyl high molecular weight gellan gum applications" Research Disclosure, Kenneth Mason Publications, Hampshire, GB, vol. 463, No. 7, Nov. 2002, XP007131518 ISSN: 0374-4353.
John Swazey: "Gellan gum in toothpaste" Research Disclosure, Kenneth Mason Publications, Hampshire, GB vol. 440, No. 130, Dec. 2000, XP007127315 ISSN: 0374-4353.
Juming Tang et al., "Compression strength and deformation of gellan gels formed with mono-and divalent cations", Carbohydrate Polymers, Applied Science Publishers, LTD. Barking, GB vol. 29, No. 1, 1996, pp. 11-16, XP004034348 ISSN: 00144-8617.

(Continued)

*Primary Examiner* — Jyothsna Venkat
(74) *Attorney, Agent, or Firm* — O'Brien Jones PLLC

(57) ABSTRACT

The present disclosure relates to a cosmetic composition comprising, in a cosmetically acceptable medium, at least one gum chosen from gellan gums and derivatives thereof, at least one fixing polymer, at least one monovalent salt, and at least one alcohol. Further disclosed herein is a process for shaping and/or holding the hairstyle using the same.

7 Claims, No Drawings

FOREIGN PATENT DOCUMENTS

| | | |
|---|---|---|
| GB | 1 169 862 | 11/1969 |
| GB | 1 572 626 | 7/1980 |
| GB | 2 384 705 A | 6/2003 |
| WO | WO 93/23009 | 11/1993 |
| WO | WO 93/23446 | 11/1993 |
| WO | WO 95/00578 | 1/1995 |
| WO | WO 01/28503 A1 | 4/2001 |

OTHER PUBLICATIONS

English language Abstract of EP 080 976 A1.

English language Derwent Abstract of EP 0 985 410 A1, Mar. 15, 2000.

* cited by examiner

COSMETIC COMPOSITION COMPRISING GELLAN GUM OR A DERIVATIVE THEREOF, A FIXING POLYMER, A MONOVALENT SALT AND AN ALCOHOL, PROCESS OF USING THE SAME

This application claims benefit of U.S. Provisional Application No. 60/562,317, filed Apr. 15, 2004, which is herein incorporated by reference in its entirety.

The present disclosure relates to an aqueous liquid cosmetic composition comprising, in a cosmetically acceptable medium, at least one gum chosen from gellan gums and derivatives thereof, at least one fixing polymer, at least one monovalent salt, and at least one alcohol. The present disclosure further relates to a process for shaping and/or holding the hairstyle wherein the cosmetic composition is used.

Cosmetic compositions for shaping and/or holding the hairstyle that are the most widely available on the cosmetics market are spray compositions comprising a solution, which may be an alcoholic solution, and at least one component, known as a fixing component, which may be polymeric resins, the function of which is to form welds between the hairs. These fixing components can be formulated as a mixture with various cosmetic adjuvants.

These cosmetic compositions may be generally packaged either in a pump-dispenser bottle or in a suitable aerosol container placed under pressure using a propellant, and the aerosol system then comprises a first liquid phase (or fluid) and a second propellant.

Once applied to the hair, the liquid phase, comprising the fixing components and a suitable solvent, dries, allowing the formation of welds for the fixing of the hair by the fixing components. The welds should be rigid enough to hold the hair, but should also be fragile enough for the user to be able, by combing or brushing the hair, to destroy them without hurting the scalp or damaging the hair.

The standard film-forming resins generally used as fixing agents in alcoholic medium have the drawback of giving the styling composition mediocre cosmetic properties. For example, the feel obtained by the use of compositions based on film-forming resins may not be very satisfactory.

To at least improve the feel of these compositions, it has often been the practice in the prior art to add silicones, but the addition of silicones to the solution does not make it possible to improve the cosmetic properties in the case of aqueous-alcoholic compositions.

The present disclosure provides, surprisingly and, for example, that the use of a combination of at least one gum chosen from gellan gums and derivatives thereof, at least one fixing polymer, at least one monovalent salt, and at least one alcohol makes it possible to improve the cosmetic properties of these compositions.

The compositions according to the present disclosure may allow good fixing and good hold of the hair, such as a styling effect that lasts throughout the day, or even for several days, which can show good resistance to moisture and can be easy to remove by shampooing.

These compositions as disclosed herein also make it possible to give the hair good cosmetic properties, such as in terms of feel (soft feel) and disentangling.

It has also been observed that the combination according to the present disclosure may allow perfect suspension of solid particles such as flakes, and perfect that the thixotropic nature of this combination may allow perfect restitution of the styling cosmetic composition when it is applied using a spray or as an aerosol.

In one embodiment of the present disclosure, an aqueous liquid cosmetic composition comprises, in a cosmetically acceptable medium, at least one gum chosen from gellan gums and derivatives thereof, at least one fixing polymer, at least one monovalent salt, and at least one alcohol.

For example, the cosmetic composition according to the disclosure is a cosmetic hair composition, such as a styling cosmetic hair composition.

Another embodiment of the present disclosure comprises a process for shaping and/or holding the hairstyle, wherein the cosmetic composition according to the disclosure is used.

A further embodiment of the disclosure relates to uses of this cosmetic composition as a styling composition for fixing and holding the hair, a haircare composition, a hair conditioning composition such as for giving the hair softness, and/or a hair makeup composition.

Thus, the present disclosure relates to the use of the cosmetic composition, as disclosed herein, for fixing the hair, holding the hair, and giving the hair cosmetic qualities.

The cosmetic composition according to the disclosure may be in the form of a spray, a mousse, or a gel.

Other embodiments, characteristics, aspects and advantages of the composition as disclosed herein will emerge even more clearly upon reading the description and the examples that follow.

Without wishing to be bound by any theory, the cosmetic compositions according to the disclosure herein may be in the form of a gel, which is known to be a three-dimensional network of molecules that holds in its mesh a large amount of solvent. The formation of such a network comprises its gelation.

The cosmetic compositions as disclosed herein may also be in the form of mousses.

As used herein, the term "styling cosmetic composition" means a composition for shaping and/or holding the hairstyle.

As used herein, the term "liquid composition" means that the viscosity of the composition as disclosed herein ranges from the viscosity of water to 50 poises such as, from the viscosity of water to 20 poises.

Further as used herein, the term "aqueous composition" means that the cosmetically acceptable medium used with the compositions according to the present disclosure is an aqueous-alcoholic and/or alcoholic medium optionally comprising at least one additional organic solvent.

The at least one alcohol used in the composition as disclosed herein is a monohydroxylated alkanol chosen from $C_1$-$C_4$ lower alcohols, for example, ethanol, isopropanol, tert-butanol, or n-butanol. In one embodiment, the alcohol is ethanol.

The at least one alcohol is present in the composition as disclosed herein in a concentration ranging from 0.1% to 99%, such as from 0.5% to 95% and for example, from 1% to 80% by weight, relative to the total weight of the composition.

Additional organic solvents that may be used in the compositions as disclosed herein are polyols such as, propylene glycol, polyol ethers, and mixtures thereof.

The amount of additional organic solvent in the compositions according to the disclosure ranges from 0% to 30% such as, from 0% and 20% by weight, relative to the total weight of the composition.

Gellan gum is a polysaccharide produced by aerobic fermentation of Sphingomonas elodea, more commonly known as Pseudomonas elodea. This linear polysaccharide comprises a sequence of the following monosaccharides: D-glucose, D-glucuronic acid, and L-rhamnose. In the native state, gellan gum is highly acylated.

The at least one gellan gum, for example, used in the compositions according to the disclosure is an at least partially deacylated gellan gum. This at least partially deacylated gellan gum may be obtained by a high-temperature alkaline treatment.

A KOH or NaOH solution can be used, for example.

The purified gellan gum sold under the trade name "Kelcogel®" by the company Kelco is suitable for preparing the compositions as disclosed herein.

The gellan gum derivatives are all products obtained by performing standard chemical reactions such as, for example, esterifications or addition of a salt of an organic or mineral acid.

An example of at least one gellan gum derivative that may be used is welan gum. Welan gum is a gellan gum modified by fermentation using the *Alcaligenes* strain ATCC 31 555. Welan gum has a repeating pentasaccharide structure formed from a main chain comprising D-glucose, D-glucuronic acid, and L-rhamnose units on which is grafted a pendent L-rhamnose or L-mannose unit.

The welan gum sold under the trade name "Kelco Crete®" by the company Kelco is suitable for preparing the compositions according to the present disclosure.

The amount of at least one gum chosen from gellan gums and derivatives thereof used in the compositions as disclosed herein ranges from 0.005% to 10%, such as from 0.01% to 5% and for example, from 0.02% to 3% by weight, relative to the total weight of the composition.

The at least one monovalent salt that may be used in the compositions according to the present disclosure are salts of monovalent cations such as alkali metal salts, ammonium salts, organic amine salts, or mixtures thereof. The monovalent cations of the alkali metals are chosen from the following cations: $Li^+$, $Na^+$, $K^+$, $Rb^+$, $Cs^+$, and $Fr^+$. In one embodiment, $Na^+$ is used in the compositions according to the present disclosure.

The counterion can be a mineral or organic anion, such as $Cl^-$, and the at least one monovalent salt that can be used, for example, is NaCl.

The concentration of the at least one monovalent salt used in the compositions according to the present disclosure ranges from 0.01% to 10% such as, from 0.05% to 5% by weight, relative to the total weight of the composition.

For example, the ratio: monovalent salt/gellan gum or derivative ranges from 1% to 50% such as, from 2% to 30%.

Any anionic, cationic, amphoteric, or nonionic fixing polymer and mixtures thereof used in the art may be used in the compositions according to the present disclosure; polymers that have only a thickening nature, such as the Carbopol or Carbomer products, are excluded.

The at least one fixing polymer may be soluble in the cosmetically acceptable medium or insoluble in this same medium, and for example, used in the form of dispersions of solid or liquid polymer particles (latices or pseudolatices).

The anionic fixing polymers generally used are polymers comprising groups derived from carboxylic acid, sulfonic acid, or phosphoric acid and have a number-average molecular weight ranging from 500 to 5,000,000.

The carboxylic groups are provided by unsaturated monocarboxylic or dicarboxylic acid monomers such as those corresponding to the formula:

wherein n is an integer ranging from 0 to 10, $A_1$ is chosen from a methylene group, optionally connected to the carbon atom of the unsaturated group, and to the neighboring methylene group when n is greater than 1, via a hetero atom such as oxygen or sulfur, $R_7$ is chosen from a hydrogen atom and a phenyl or benzyl group, $R_8$ is chosen from a hydrogen atom and a lower alkyl and carboxyl group, $R_9$ is chosen from a hydrogen atom, a lower alkyl group, and a —$CH_2$—COOH, phenyl and benzyl group.

In the abovementioned formula, a lower alkyl group is chosen from, for example, a group having 1 to 4 carbon atoms such as, methyl and ethyl.

The anionic fixing polymers comprising carboxylic groups, for example, are chosen from:

A) acrylic and methacrylic acid homo- and copolymers, and salts thereof and for example, the products sold under the names Versicol® E or K by the company Allied Colloid and Ultrahold® by the company BASF, the copolymers of acrylic acid and of acrylamide sold in the form of their sodium salts under the names Reten 421, 423 or 425 by the company Hercules, the sodium salts of polyhydroxycarboxylic acids.

B) Copolymers of acrylic and methacrylic acid with a monoethylenic monomer such as ethylene, styrene, vinyl esters, acrylic and methacrylic acid esters, optionally grafted onto a polyalkylene glycol such as, polyethylene glycol and optionally crosslinked. Such polymers are described, for example, in French Patent No. 1 222 944 and German Patent Application No. 2 330 956, the copolymers of this type comprising an optionally N-alkylated and/or hydroxyalkylated acrylamide unit in their chain as described, for example, in Luxembourg Patent Application Nos. 75370 and 75371 and sold under the name Quadramer by the company American Cyanamid. Mention may also be made, for example, of copolymers of acrylic acid and of $C_1$-$C_4$ alkyl methacrylate and terpolymers of vinylpyrrolidone, of acrylic acid and of methacrylate of $C_1$-$C_{20}$ alkyl, for example of lauryl, such as the product sold by the company ISP under the name Acrylidone® LM and methacrylic acid/ethyl acrylate/tert-butyl acrylate terpolymers such as, the product sold under the name Luvimer® 100 P by the company BASF.

Mention may also be made, for example, of methacrylic acid/acrylic acid/ethyl acrylate/methyl methacrylate copolymers as an aqueous dispersion, sold under the name Amerhold® DR 25 by the company Amerchol.

C) Crotonic acid copolymers, such as those comprising vinyl acetate and propionate units in their chain and optionally other monomers such as allylic esters and methallylic esters, vinyl ether and vinyl ester of a linear and branched saturated carboxylic acid with a long hydrocarbon chain such as, those comprising at least 5 carbon atoms, it being possible for these polymers optionally to be grafted or crosslinked, or alternatively another vinyl, allylic and methallylic ester monomer of an α- and β-cyclic carboxylic acid. Such polymers are described, inter alia, in French Patent Nos. 1 222 944, 1 580 545, 2 265 782, 2 265 781, 1 564 110, and 2 439 798. Commercial products falling into this class are the resins 28-29-30, 26-13-14 and 28-13-10 sold by the company National Starch.

D) Copolymers derived from $C_4$-$C_8$ monounsaturated carboxylic acids and anhydrides chosen from:

copolymers comprising (i) at least one maleic, fumaric and itaconic acids and anhydrides and (ii) at least one monomer chosen from vinyl esters, vinyl ethers, vinyl halides, phenylvinyl derivatives, acrylic acid and its esters, the anhydride functions of these copolymers optionally being monoesterified or monoamidated. Such polymers are described, for example, in U.S. Pat. Nos. 2,047,398, 2,723,248, and 2,102,113, and GB Patent No. 839 805 and for example, those sold under the names Gantrez® AN or ES by the company ISP. Commercial products are:

copolymers comprising (i) at least one maleic, citraconic and itaconic anhydride units and (ii) at least one monomer chosen from allylic and methallylic esters optionally comprising at least one acrylamide, methacrylamide, (x-olefin, acrylic and methacrylic ester, acrylic and methacrylic acid and vinylpyrrolidone groups in their chain, the anhydride functions of these copolymers optionally being monoesterified or monoamidated.

These polymers are described, for example, in French Patent Nos. 2 350 384 and 2 357 241.

E) Polyacrylamides comprising carboxylate groups.

The homopolymers and copolymers comprising sulfonic groups are polymers comprising at least one unit chosen from vinylsulfonic, styrenesulfonic, naphthalenesulfonic, and acrylamidoalkylsulfonic units.

These polymers can be chosen, for example, from:

polyvinylsulfonic acid salts having a molecular weight of ranging from 1000 to 100,000, as well as the copolymers with an unsaturated comonomer such as acrylic and methacrylic acids and their esters, as well as acrylamide and its derivatives, vinyl ethers and vinylpyrrolidone;

polystyrenesulfonic acid salts such as the sodium salts that are sold, for example, under the names Flexan® 500 and Flexan® 130 by National Starch. These compounds are described in French Patent No. FR 2 198 719;

polyacrylamidesulfonic acid salts, such as those mentioned in U.S. Pat. No. 4,128,631 and for example, polyacrylamidoethylpropanesulfonic acid sold under the name Cosmedia Polymer HSP 1180 by Henkel.

As another anionic fixing polymer that can be used according to the present disclosure, mention may be made of the branched block anionic polymer sold under the name Fixate G-100 by the company Noveon.

According to the present disclosure, the anionic fixing polymers are, for example, chosen from acrylic acid copolymers, such as the acrylic acid/ethyl acrylate/N-tert-butylacrylamide terpolymers sold, for example, under the name Ultrahold® Strong by the company BASF; copolymers derived from crotonic acid, such as vinyl acetate/vinyl tert-butylbenzoate/crotonic acid terpolymers and the crotonic acid/vinyl acetate/vinyl neododecanoate terpolymers sold, for example, under the name Resin 28-29-30 by the company National Starch; polymers derived from maleic, fumaric and itaconic acids and anhydrides with vinyl esters, vinyl ethers, vinyl halides, phenylvinyl derivatives and acrylic acid and esters thereof, such as the methyl vinyl ether/monoesterified maleic anhydride copolymers sold, for example, under the name Gantrez® by the company ISP; the copolymers of methacrylic acid and of methyl methacrylate sold under the name Eudragit® L by the company Rohm Pharma; the copolymers of methacrylic acid and of ethyl acrylate sold, for example, under the name Luvimer® MAEX or MAE by the company BASF; the vinyl acetate/crotonic acid copolymers sold under the name Luviset CA 66 by the company BASF; the vinyl acetate/crotonic acid copolymers grafted with polyethylene glycol sold under the name Aristoflex® A by the company BASF; and the polymer sold under the name Fixate G-100 by the company Noveon.

Among the anionic fixing polymers mentioned above, mention may be made, for example, to use the methyl vinyl ether/monoesterified maleic anhydride copolymers sold under the name Gantrez® ES 425 by the company ISP; the acrylic acid/ethyl acrylate/N-tert-butylacrylamide terpolymers sold under the name Ultrahold® Strong by the company BASF; the copolymers of methacrylic acid and of methyl methacrylate sold under the name Eudragit® L by the company Rohm Pharma; the vinyl acetate/vinyl tert-butylbenzoate/crotonic acid terpolymers and the crotonic acid/vinyl acetate/vinyl neododecanoate terpolymers sold under the name Resin 28-29-30 by the company National Starch; the copolymers of methacrylic acid and of ethyl acrylate sold. under the name Luvimer® MAEX or MAE by the company BASF; the vinylpyrrolidone/acrylic acid/lauryl methacrylate terpolymers sold under the name Acrylidone® LM by the company ISP; and the polymer sold under the name Fixate G-100 by the company Noveon.

The cationic fixing film-forming polymers that may be used according to the present disclosure are, for example, chosen from polymers comprising primary, secondary, tertiary, and/or quaternary amine groups forming part of the polymer chain or directly attached thereto, and having a molecular weight ranging from 500 to 5,000,000 such as, from 1,000 and 3,000,000.

Among these polymers, mention may be made, for example, to the following cationic polymers chosen from:

(1) homopolymers and copolymers derived from acrylic and methacrylic esters and amides and comprising at least one of the units of the following formulae:

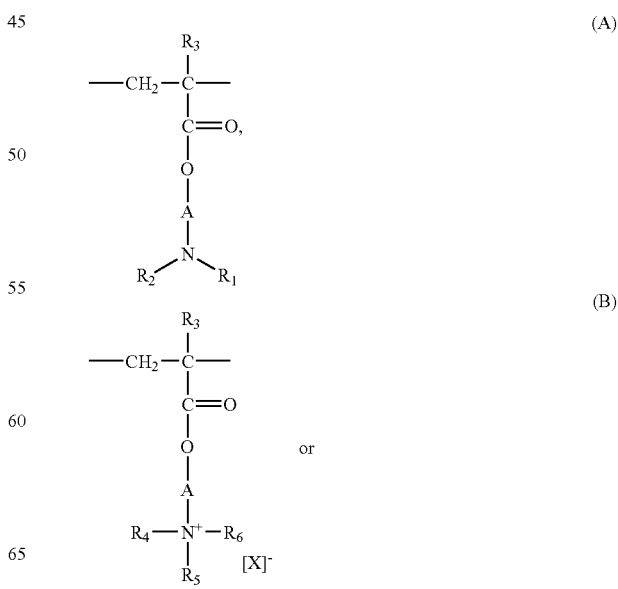

-continued

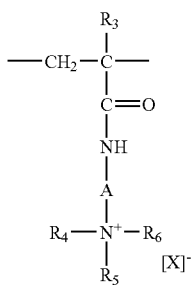

(C)

wherein:

$R_3$ is chosen from a hydrogen atom and a $CH_3$ radical;

A is a group chosen from a linear and branched alkyl group comprising 1 to 6 carbon atoms and a hydroxyalkyl group comprising 1 to 4 carbon atoms;

$R_4$, $R_5$ and $R_6$, which may be identical or different, are chosen from alkyl groups having from 1 to 18 carbon atoms and benzyl radicals;

$R_1$ and $R_2$, which may be identical or different, are chosen from hydrogen atoms and alkyl groups having from 1 to 6 carbon atoms;

X is chosen from a methosulfate anion and a halide such as, chloride or bromide.

The copolymers of the family (1) also comprise at least one comonomer unit that may be chosen from the family of acrylamides, methacrylamides, diacetone acrylamides, acrylamides, and methacrylamides substituted on the nitrogen with lower ($C_1$-$C_4$) alkyl groups, groups derived from acrylic and methacrylic acids and esters thereof, vinyllactams such as, vinylpyrrolidone and vinylcaprolactam, and vinyl esters.

Thus, among these copolymers of the family (1), mention may be made, for example, to:

copolymers of acrylamide and of dimethylaminoethyl methacrylate quaternized with dimethyl sulfate and with a dimethyl halide, such as the one sold under the name Hercofloc® by the company Hercules, copolymers of acrylamide and of methacryloyloxyethyltrimethylammonium chloride, described, for example, in European Patent Application No. EP-A-080 976 and sold under the name Bina Quat P 100 by the company Ciba Geigy, copolymers of acrylamide and of methacryloyloxyethyltrimethylammonium methosulfate, such as the product sold under the name Reten by the company Hercules, quaternized and non-quaternized vinylpyrrolidone/dialkylaminoalkyl acrylate and methacrylate copolymers, such as the products sold under the name "Gafquat®" by the company ISP, such as, for example, "Gafquat® 734" and "Gafquat® 755", and alternatively, the products known as "Copolymer® 845, 958 and 937". These polymers are described in detail in French Patent Nos. 2 077 143 and 2 393 573, fatty-chain polymers comprising a vinylpyrrolidone unit, such as the products sold under the name Styleze W20 and Styleze W10 by the company ISP, dimethylaminoethyl methacrylate/vinylcaprolactam/vinylpyrrolidone terpolymers, such as the product sold under the name Gaffix VC 713 by the company ISP, and quaternized vinylpyrrolidone/dimethylaminopropylmethacrylamide copolymers, such as the product sold under the name "Gafquat® HS 100" by the company ISP;

(2) cationic polysaccharides, for example, comprising quaternary ammonium, such as, those described in U.S. Pat. Nos. 3,589,578 and 4,031,307, such as guar gums comprising trialkylammonium cationic groups. Such products are sold, for example, under the trade names Jaguar C13S, Jaguar C15 and Jaguar C17 by the company Meyhall;

(3) quaternary copolymers of vinylpyrrolidone and of vinylimidazole;

(4) chitosans and salts thereof; the salts that can be used are, for example, chosen from chitosan acetate, lactate, glutamate, gluconate, and pyrrolidonecarboxylate.

Among these compounds, mention may be made, for example, to chitosan having a degree of deacetylation of 90.5% by weight, sold under the name. Kytan Brut Standard by the company Aber Technologies, and chitosan pyrrolidonecarboxylate sold under the name Kytamer® PC by the company Amerchol.

(5) Cationic cellulose derivatives such as, copolymers of cellulose and of cellulose derivatives grafted with a water-soluble monomer comprising a quaternary ammonium, and disclosed, for example, in U.S. Pat. No.4,131,576, such as hydroxyalkylcelluloses, for example, hydroxymethyl-, hydroxyethyl- and hydroxy-propylcelluloses grafted such as, with a methacryloyloxyethyltrimethylammonium, methacrylamidopropyltrimethylammonium, and dimethyidiallylammonium salt.

The products sold that may correspond to this definition are, for example, the products sold under the name "Celquat L 200" and "Celquat H 100" by the company National Starch.

The amphoteric fixing polymers that can be used in accordance with the present disclosure can be chosen from polymers comprising units B and C distributed randomly in the polymer chain, wherein B is chosen from a unit derived from a monomer comprising at least one basic nitrogen atom and C is chosen from a unit derived from an acid monomer comprising at least one group chosen from carboxylic and sulfonic groups, or alternatively B and C can denote groups derived from carboxybetaine and sulfobetaine zwitterionic monomers;

B and C can also be chosen from a cationic polymer chain comprising primary, secondary, tertiary and quaternary amine groups, wherein at least one of the amine groups bears a group chosen from carboxylic and sulfonic groups connected via a hydrocarbon group or alternatively, B and C form part of a chain of a polymer comprising an x,p-dicarboxylic ethylene unit wherein at least one of the carboxylic groups is reactive with a polyamine comprising at least one primary or secondary amine groups.

The amphoteric fixing polymers corresponding to the definition given above that are, for example, chosen from the following polymers:

(1) copolymers having acidic vinyl and basic vinyl units, such as those resulting from the copolymerization of a monomer derived from a vinyl compound bearing a carboxylic group such as, for example, acrylic acid, methacrylic acid, maleic acid, α-chloroacrylic acid, and a basic monomer derived from a substituted vinyl compound comprising at least one basic atom, such as, for example, dialkylaminoalkyl methacrylate and acrylate, dialkylaminoalkylmethacrylamide and -acrylamide. Such compounds are described in U.S. Pat. No. 3,836,537.

(2) Polymers comprising units derived from:
a) at least one monomer chosen from acrylamides and methacrylamides substituted on the nitrogen atom with an alkyl group,
b) at least one acidic comonomer comprising at least one reactive carboxylic group, and c) at least one basic comonomer such as, esters comprising primary, secondary, tertiary and quaternary amine substituents of acrylic and methacrylic acids and the product of quaternization of dimethylaminoethyl methacrylate with dimethyl or diethyl sulfate.

The N-substituted acrylamides or methacrylamides that may be mentioned, for example, are compounds wherein the alkyl groups comprising from 2 to 12 carbon atoms and for example, N-ethylacrylamide, N-tert-butylacrylamide, N-tert-octylacrylamide, N-octylacrylamide, N-decylacrylamide, N-dodecylacrylamide, and the corresponding methacrylamides.

The acidic comonomers are chosen, for example, from acrylic acid, methacrylic acid, crotonic acid, itaconic acid, maleic acid, and fumaric acid and alkyl monoesters, having 1 to 4 carbon atoms, of maleic and fumaric acids and anhydrides.

For example, comonomers may be aminoethyl, butylaminoethyl, N,N'-dimethylaminoethyl, and N-tert-butylaminoethyl methacrylates.

The copolymers whose CTFA (4th edition, 1991) name is octylacryl-amide/acrylates/butylaminoethyl methacrylate copolymer, such as the products sold under the name Amphomer® or Lovocryl® 47 by the company National Starch, may be used herein.

(3) Crosslinked and acylated polyamino amides partially and totally derived from polyamino amides of general formula:

$$\{CO-R_{10}-CO-Z\}-\quad\quad (II)$$

wherein $R_{10}$ is chosen from a divalent group derived from a saturated dicarboxylic acid, a mono- and dicarboxylic aliphatic acid comprising an ethylenic double bond, an ester of a lower alkanol, having 1 to 6 carbon atoms, of these acids, and a group derived from the addition of any one of the saturated discarboxylic acid, a mono and dicarboxylic aliphatic acids to a bis(primary) and bis(secondary) amine, and Z is chosen from a group derived from a bis(primary), mono- and bis(secondary) polyalkylene-polyamine and for example, is chosen from:

a) in proportions of from 60 mol % to 100 mol %, the group:

$$-\underset{H}{N}-\{(CH_2)_x-\underset{H}{N}\}_p-\quad\quad (III)$$

wherein x=2 and p=2 or 3, or alternatively x=3 and p=2, this group being derived from diethylenetriamine, from triethylenetetraamine or from dipropylenetriamine;

b) in proportions of from 0 mol % to 40 mol %, the group (III) above wherein x=2 and p=1 and wherein derived from ethylenediamine, or the group derived from piperazine:

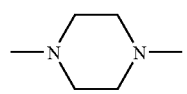

c) in proportions of from 0 to 20 mol %, the —NH(CH$_2$)$_6$—NH— group being derived from hexamethylenediamine, these polyamino amides being crosslinked by addition reaction of a difunctional crosslinking agent chosen from epihalohydrins, diepoxides, dianhydrides and bis-unsaturated derivatives, using from 0.025 mol to 0.35 mol of crosslinking agent per amine group of the polyamino amide and acylated by the action of acids chosen from acrylic acid, chloroacetic acid and an alkane sultone, and salts thereof.

The saturated carboxylic acids are, for example, chosen from acids having 6 to 10 carbon atoms, such as adipic acid, 2,2,4-trimethyladipic acid, and 2,4,4-trimethyladipic acid, terephthalic acid, acids comprising an ethylenic double bond such as, for example, acrylic acid, methacrylic acid and itaconic acid.

The alkane sultones that may be used in the acylation are, for example, propane sultone or butane sultone; the salts of the acylating agents are, for example, the sodium or potassium salts.

(4) Polymers comprising zwitterionic units of formula:

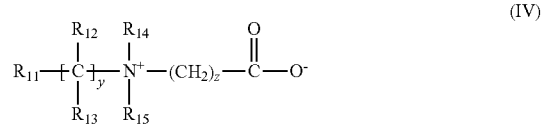

wherein $R_{11}$ is chosen from a polymerizable unsaturated group such as, an acrylate, methacrylate, acrylamide and methacrylamide group, y and z are each an integer ranging from 1 to 3, $R_{12}$ and $R_{13}$ are chosen from hydrogen atoms, methyl, ethyl and propyl groups, $R_{14}$ and $R_{15}$ are chosen from hydrogen atoms and alkyl groups such that the sum of the carbon atoms in $R_{14}$ and $R_{15}$ does not exceed 10.

The polymers comprising such units can also comprise units derived from non-zwitterionic monomers such as, dimethyl- or diethylaminoethyl acrylate or methacrylate or alkyl acrylates or methacrylates, acrylamides or methacrylamides or vinyl acetate.

By way of example, mention may be made of the copolymers of methyl methacrylate/methyl dimethylcarboxymethylammonioethyl methacrylate such as, the product sold under the name Diaformer Z301 by the company Sandoz.

(5) Polymers derived from chitosan comprising monomer units corresponding to the following formulae:

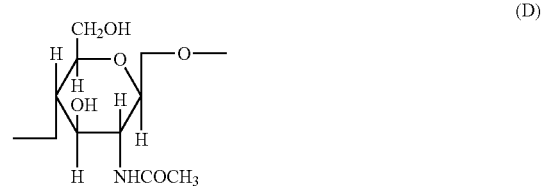

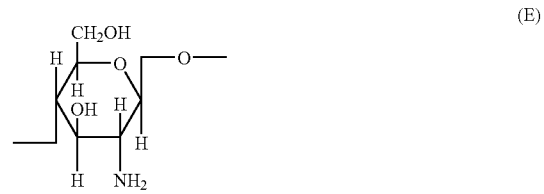

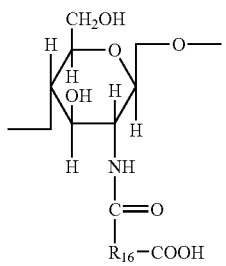
(F)

the unit (D) is present in proportions ranging from 0% to 30%, the unit (E) in proportions ranging from 5% to 50% and the unit (F) in proportions ranging from 30% to 90%, it being understood that, in this unit (F), $R_{16}$ is chosen from a group of formula:

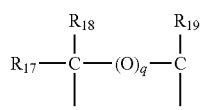

wherein, if q=0, $R_{17}$, $R_{18}$ and $R_{19}$, which may be identical or different, are chosen from hydrogen atoms, methyl, hydroxyl, acetoxy and amino residues, monoalkylamine residues and dialkylamine residues that are optionally interrupted by at least one nitrogen atom and/or optionally substituted with at least one amine, hydroxyl, carboxyl, alkylthio and sulfonic groups, alkylthio residues wherein the alkyl group bears an amino residue, at least one of the groups $R_{17}$, $R_{18}$ and $R_{19}$ being, in this case, a hydrogen atom;

or, if q=1, $R_{17}$, $R_{18}$ and $R_{19}$ each is chosen from a hydrogen atom, as well as the salts formed by these compounds with bases and acids.

(6) Polymers corresponding to the general formula (V) that are described, for example, in French Patent No. 1 400 366:

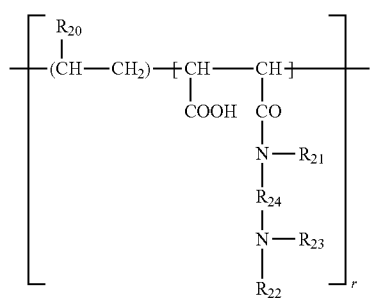
(V)

wherein $R_{20}$ is chosen from a hydrogen atom, a $CH_3O$, $CH_3CH_2O$ and phenyl group, $R_{21}$ is chosen from a hydrogen atom and a lower alkyl group such as, methyl and ethyl, $R_{22}$ is chosen from a hydrogen atom and a $C_1$-$C_6$ lower alkyl group such as, methyl and ethyl, $R_{23}$ is chosen from a $C_1$-$C_6$ lower alkyl group such as, methyl and ethyl and a group corresponding to the formula: —$R_{24}$—$N(R_{22})_2$, $R_{24}$ is chosen from a —$CH_2$—$CH_2$—, —$CH_2$—$CH_2$—$CH_2$— and —$CH_2$—$CH(CH_3)$— group, $R_{22}$ having the meanings mentioned above, r is such that the molecular weight of the polymer ranges from 500 to 6,000,000 and for example, from 1,000 to 1, 000, 000.

(7) Polymers derived from the N-carboxyalkylation of chitosan, such as N-carboxymethylchitosan or N-carboxybutylchitosan sold under the name "Evalsan" by the company Jan Dekker.

(8) Amphoteric polymers of the type -D-X-D-X- chosen from:

a) polymers obtained by the action of chloroacetic acid and/or sodium chloroacetate on compounds comprising at least one unit of formula:

-D-X-D-X-D- (VI)

wherein D is chosen from a group

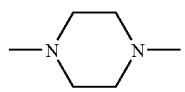

and X is chosen from the symbol E and E', E and E', which may be identical or different, are chosen from divalent groups that are alkylene groups with a straight or branched chain comprising up to 7 carbon atoms in the main chain, which is unsubstituted or substituted with hydroxyl groups and which can comprise, in addition to the oxygen, nitrogen and sulfur atoms, from 1 to 3 aromatic and/or heterocyclic rings; the oxygen, nitrogen and sulfur atoms being present in the form chosen from ether, thioether, sulfoxide, sulfone, sulfonium, alkylamine and alkenylamine groups, hydroxyl, benzylamine, amine oxide, quaternary ammonium, amide, imide, alcohol, ester and/or urethane groups.

b) Polymers of formula:

-D-X-D-X- (VI')

wherein D denotes a group

and X is chosen from the symbol E and E' and at least one E'; E having the meaning given above and E' is chosen from a divalent group that is an alkylene group with a straight and branched chain having up to 7 carbon atoms in the main chain, which is unsubstituted or substituted, with at least one hydroxyl group and comprising at least one nitrogen atom, the nitrogen atom being substituted with an alkyl chain that is optionally interrupted by an oxygen atom and necessarily comprising at least one carboxyl function or at least one hydroxyl function and betainized by reaction with chloroacetic acid or sodium chloroacetate.

(9) ($C_1$-$C_5$)alkyl vinyl ether/maleic anhydride copolymers partially modified by semiamidation with an N,N-dialkylaminoalkylamine such as, N,N-dimethylamino-propylamine or by semiesterification with an N,N-dialkylaminoalkanol. These copolymers can also comprise other vinyl comonomers such as, vinylcaprolactam.

Of the amphoteric fixing polymers described above, mention may be made, for example, to those of family (3), such as the copolymers whose CTFA name is octylacrylamide/acrylates/butylaminoethyl methacrylate copolymer, such as the products sold under the names Amphomer®, Amphomer® LV 71 or Lovocryl® 47 by the company National Starch and those of family (4) such as the copolymers of methyl methacrylate/methyl dimethylcarboxymethylammonioethyl methacrylate, sold, for example, under the name Diaformer® Z301 by the company Sandoz.

The nonionic fixing polymers that may be used according to the present disclosure are chosen, for example, from:
polyalkyloxazolines;
vinyl acetate homopolymers;
vinyl acetate copolymers, for example, copolymers of vinyl acetate and of acrylic ester; copolymers of vinyl acetate and of ethylene; copolymers of vinyl acetate and of maleic ester, for example, of dibutyl maleate;
homopolymers and copolymers of acrylic esters, for example, copolymers of alkyl acrylates and of alkyl methacrylates, such as the products sold by the company Rohm & Haas under the names Primal® AC-261 K and Eudragit® NE 30 D, by the company BASF under the name 8845, or by the company Hoechst under the name Appretan® N9212;
copolymers of acrylonitrile and of a nonionic monomer chosen, for example, from butadiene and alkyl (meth) acrylates; mention may be made of the products sold under the name CJ 0601 B by the company Rohm & Haas;
styrene homopolymers;
styrene copolymers, for example, copolymers of styrene and of alkyl (meth)acrylate, such as the products Mowilith® LDM 6911, Mowilith® DM 611 and Mowilith® LDM 6070 sold by the company Hoechst, and the products Rhodopas® SD 215 and Rhodopas® DS 910 sold by the company Rhône-Poulenc; copolymers of styrene, of alkyl methacrylate and of alkyl acrylate; copolymers of styrene and of butadiene; or copolymers of styrene, of butadiene and of vinylpyridine;
polyamides;
vinyllactam homopolymers other than vinylpyrrolidone homopolymers, such as, the polyvinylcaprolactam sold under the name Luviskol® Plus by the company BASF; and
vinyllactam copolymers such as a poly(vinylpyrrolidone/ vinyllactam) copolymer sold under the trade name Luvitec® VPC 55K65W by the company BASF, poly (vinylpyrrolidone/vinyl acetate) copolymers, such as those sold under the name PVPVA® S630L by the company ISP, Luviskol® VA 73, VA 64, VA 55, VA 37 and VA 28 by the company BASF; and poly(vinylpyrrolidone/vinyl acetate/vinyl propionate) terpolymers, for example, the product sold under the name Luviskol® VAP 343 by the company BASF.

The alkyl groups of the nonionic polymers mentioned above, for example, comprise from 1 to 6 carbon atoms.

According to the present disclosure, it is also possible to use fixing polymers of grafted silicone type comprising a polysiloxane portion and a portion comprising a non-silicone organic chain, at least one of the two portions comprising the main chain of the polymer, and the other being grafted onto the main chain.

These polymers are described, for example, in Patent Application Nos. EP-A-0 412 704, EP-A-0 412 707, EP-A-0 640 105 and WO 95/00578, EP-A-0 582 152 and WO 93/23009 and U.S. Pat. Nos. 4,693,935, 4,728,571, and 4,972,037.

These polymers may be amphoteric, anionic or nonionic, and are, for example, anionic or nonionic.

Such polymers are, for example, copolymers that can be obtained by free radical polymerization from the monomer mixture formed from:
a) 50% to 90% by weight of tert-butyl acrylate;
b) 0% to 40% by weight of acrylic acid;
c) 5% to 40% by weight of a silicone macromer of formula:

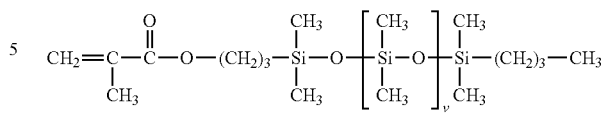

wherein v is a number ranging from 5 to 700; the weight percentages being calculated relative to the total weight of the monomers.

Other examples of grafted silicone polymers are, for example, polydimethyl-siloxanes (PDMSs) onto which are grafted, via a thiopropylene-type connecting chain unit, mixed polymer units of the poly(meth)acrylic acid type and of the polyalkyl (meth)acrylate type and polydimethylsiloxanes (PDMSS) onto which are grafted, via a thiopropylene-type connecting chain unit, polymer units of the polyisobutyl (meth)acrylate type.

Another type of silicone fixing polymer that may be mentioned, for example, is the product Luviflexe Silk, sold by the company BASF.

Functionalized or non-functionalized, silicone or non-silicone, cationic, nonionic, anionic or amphoteric polyurethanes or mixtures thereof may also be used as fixing polymers.

The polyurethanes, for example, disclosed herein according to the present disclosure are those disclosed in Patent Nos. EP 0 751 162, EP 0 637 600, EP 0 648 485 and FR 2 743 297, and Patent Nos. EP 0 656 021 and WO 94/03510 from the company BASF and EP 0 619 111 from the company National Starch.

Polyurethanes that are, for example, suitable for use with the present disclosure, mention may be made of the products sold under the names Luviset Pur® and Luviset® Si—Pur by the company BASF.

The concentration of fixing polymer(s) used in the compositions according to the present disclosure ranges from 0.1% to 20% and for example, from 0.5% to 10% by weight, relative to the total weight of the composition.

The styling composition according to the present disclosure may also comprise at least one adjuvant chosen from silicones in soluble, dispersed and microdispersed form, nonionic, anionic, cationic and amphoteric surfactants, nonionic, anionic, cationic and amphoteric additional polymers other than the fixing polymers used in the compositions according to the disclosure, ceramides, pseudoceramides, vitamins and provitamins, including panthenol, plant, animal, mineral and synthetic oils, waxes other than ceramides and pseudoceramides, silicone-based or non-silicone-based water-soluble and liposoluble sunscreens, solid particles, for example, colored or uncolored, mineral and organic pigments, nacreous agents and opacifiers, flakes, active particles, dyes, sequestering agents, plasticizers, solubilizers, acidifying agents, basifying agents, neutralizers, mineral and organic thickeners, antioxidants, hydroxy acids, penetrating agents, fragrances, and preserving agents.

A person skilled in the art will take care to select the optional additives and the amount thereof such that they do not harm the properties of the compositions according to the present disclosure.

These additives are present in the composition according to the disclosure in an amount ranging from 0% to 20% by weight, relative to the total weight of the composition.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The example that follows illustrates the present invention and should not in any way be considered as limiting the invention.

EXAMPLE

A composition formulated as a spray in a pump-dispenser bottle was prepared; the contents of the various constituents in g/100 g were as follows:

| Constituent | g/100 g |
|---|---|
| UltraHold ® Strong sold by BASF | 2 |
| AMP(aminomethylpropanol) | 0.2 |
| Gellan gum | 1 |
| NaCl | 2 |
| Flakes (Mica and titanium oxide) | 0.5 |
| Distilled water | 45 |
| Fragrance | qs |
| Alcohol | qs 100 |

UltraHold® Strong sold by BASF is an acrylic acid/ethyl acrylate/N-tert-butylacrylamide anionic fixing terpolymer.

What is claimed is:

1. An aqueous liquid cosmetic composition comprising, in a cosmetically acceptable medium,
   a partially deacylated gellan gum present in an amount ranging from 0.02% to 1% by weight, relative to the total weight of the aqueous liquid cosmetic composition,
   a fixing polymer of acrylic acid/ethyl acrylate/N-tert-butylacrylamide terpolymers and present in an amount ranging from 0.5% to 10% by weight, relative to the total weight of the aqueous liquid cosmetic composition,
   NaCl present in an amount ranging from 0.05% to 5% by weight, relative to the total weight of the aqueous liquid cosmetic composition, and
   ethanol present in an amount ranging from 1% to 80% by weight, relative to the total weight of the aqueous liquid cosmetic composition,
   wherein the aqueous liquid cosmetic composition is a styling composition for the hair.

2. The aqueous liquid cosmetic composition according to claim 1, further comprising at least one adjuvant chosen from silicones in soluble, dispersed and microdispersed form, nonionic, anionic, cationic and amphoteric surfactants, nonionic, anionic, cationic and amphoteric additional polymers, ceramides, pseudoceramides, vitamins and provitamins, plant, animal, mineral and synthetic oils, waxes other than ceramides and pseudoceramides, silicone-based and non-silicone based water-soluble and liposoluble sunscreens, solid particles, mineral and organic pigments, nacreous agents and opacifiers, flakes, active particles, dyes, sequestering agents, plasticizers, solubilizers, acidifying agents, basifying agents, neutralizers, mineral and organic thickeners, antioxidants, hydroxyl acids, penetrating agents, fragrances, and preserving agents.

3. The aqueous liquid cosmetic composition according to claim 1, wherein the aqueous liquid cosmetic composition is in a form of a spray.

4. The aqueous liquid cosmetic composition according to claim 1, wherein the aqueous liquid cosmetic composition is in a form of a gel.

5. The aqueous liquid cosmetic composition according to claim 1, wherein the aqueous liquid cosmetic composition is in a form of a mousse.

6. A process for shaping and/or holding a hairstyle comprising:
   applying to hair an aqueous liquid cosmetic composition comprising, in a cosmetically acceptable medium, a partially deacylated gellan gum present in an amount ranging from 0.02% to 1% by weight, relative to the total weight of the aqueous liquid cosmetic composition, a fixing polymer of acrylic acid/ethyl acrylate/N-tert-butylacrylamide terpolymers and present in an amount ranging from 0.5% to 10% by weight, relative to the total weight of the aqueous liquid cosmetic composition, NaC present in an amount ranging from 0.05% to 5% by weight, relative to the total weight of the aqueous liquid cosmetic composition, and ethanol present in an amount ranging from 1% to 80% by weight, relative to the total weight of the aqueous liquid cosmetic composition.

7. The process according to claim 6, wherein the aqueous liquid cosmetic composition is a styling composition for fixing and holding the hair.

* * * * *

UNITED STATES PATENT AND TRADEMARK OFFICE
CERTIFICATE OF CORRECTION

| | | |
|---|---|---|
| PATENT NO. | : 8,246,940 B2 | Page 1 of 1 |
| APPLICATION NO. | : 10/990516 | |
| DATED | : August 21, 2012 | |
| INVENTOR(S) | : Laurence Marie et al. | |

It is certified that error appears in the above-identified patent and that said Letters Patent is hereby corrected as shown below:

IN THE CLAIMS:

At col. 16, in claim 6, line 44, "NaC" should be -- NaCl --.

Signed and Sealed this
First Day of January, 2013

David J. Kappos
*Director of the United States Patent and Trademark Office*